United States Patent
Morales

[19]

[11] Patent Number: 5,931,851
[45] Date of Patent: Aug. 3, 1999

[54] METHOD AND APPARATUS FOR RUBBER-TUBE CRIMPING TOOL WITH PREMOUNT STENT

[75] Inventor: Stephen A. Morales, Mountain View, Calif.

[73] Assignee: Advanced Cardiovascular Systems, Inc., Santa Clara, Calif.

[21] Appl. No.: 09/063,587

[22] Filed: Apr. 21, 1998

[51] Int. Cl.⁶ .................................................. A61M 29/00
[52] U.S. Cl. ............................ 606/194; 606/198; 29/235
[58] Field of Search .................................... 606/198, 194, 606/192, 108; 623/1; 604/96; 29/282, 234, 235

[56] References Cited

U.S. PATENT DOCUMENTS

| | | |
|---|---|---|
| 696,289 | 3/1902 | Williams . |
| 4,468,224 | 8/1984 | Enzmann et al. . |
| 4,576,142 | 3/1986 | Schiff . |
| 4,644,936 | 2/1987 | Schiff . |
| 4,681,092 | 7/1987 | Cho et al. . |
| 4,697,573 | 10/1987 | Schiff . |
| 4,901,707 | 2/1990 | Schiff . |
| 4,907,336 | 3/1990 | Gianturco . |
| 5,132,066 | 7/1992 | Charlesworth et al. . |
| 5,133,732 | 7/1992 | Wiktor . |
| 5,183,085 | 2/1993 | Timmermans . |
| 5,189,786 | 3/1993 | Ishikawa et al. . |
| 5,437,083 | 8/1995 | Williams et al. . |
| 5,546,646 | 8/1996 | Williams et al. . |
| 5,626,604 | 5/1997 | Cottone, Jr. . |
| 5,630,830 | 5/1997 | Verbeek . |
| 5,653,691 | 8/1997 | Rupp et al. . |
| 5,738,674 | 4/1998 | Williams et al. . |
| 5,746,764 | 5/1998 | Green et al. . |
| 5,783,227 | 7/1998 | Dunham . |
| 5,785,715 | 7/1998 | Schatz . |
| 5,836,952 | 11/1998 | Davis et al. ............................ 606/108 |

FOREIGN PATENT DOCUMENTS

| | | |
|---|---|---|
| WO 98/14120 | 4/1998 | WIPO . |
| WO 98/19633 | 5/1998 | WIPO . |

OTHER PUBLICATIONS

U.S. Patent Application Serial No. 08/795,335 filed Feb. 4, 1997.
U.S. Patent Application Serial No. 08/837,771 filed Apr. 22, 1997.
U.S. Patent Application Serial No. 08/089,936 filed Jul. 15, 1997.
U.S. Patent Application Serial No. 08/962,632 filed Nov. 3, 1997.
*The eXTraordinary Stent*, C.R. Bard Brochure (Undated).

*Primary Examiner*—Michael Buiz
*Assistant Examiner*—Julian W. Woo
*Attorney, Agent, or Firm*—Fulwider Patton Lee & Utecht, LLP

[57] ABSTRACT

A stent crimping tool for firmly and uniformly crimping a stent onto a balloon catheter is constructed from a housing containing a silicone tube wherein the silicone tube is compressed by a thumb screw that is threaded into one end of the housing. The silicone tube has a passage containing a premounted uncrimped stent. The balloon catheter is inserted through the thumb screw and aligned with the stent inside the tube. Both ends of the silicone tubing are tapered and engage a tapered internal end inside the housing and a tapered recess inside the thumb screw. Advancing the thumb screw decreases the length of the silicone tubing and reshapes it so that the inside diameter of the passage decreases thereby crimping the stent onto the balloon. In an alternative embodiment, the opposite end of the housing is fitted with a second thumb screw. Further, the silicone tubing can be separated into two discrete segments by an annular washer located at a mid-point along the length of the silicone tube.

20 Claims, 3 Drawing Sheets

METHOD AND APPARATUS FOR RUBBER-TUBE CRIMPING TOOL WITH PREMOUNT STENT

BACKGROUND OF THE INVENTION

The present invention relates to an apparatus for loading a tubular graft, such as a stent, onto the distal end of a catheter assembly of the kind used, for example, in percutaneous transluminal coronary angioplasty (PTCA) or percutaneous transluminal angioplasty (PTA) procedures.

In typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop over time, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the lesion. The stent is crimped tightly onto the balloon portion of the catheter and transported in its delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and probably through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing blood clots in the vasculature, including thrombosis. Therefore, it is important to ensure the proper crimping of a stent onto a catheter in a uniform and reliable manner.

This crimping is often done by hand, which can be unsatisfactory due to the uneven application of force resulting in non-uniform crimps. In addition, it is difficult to visually judge when a uniform and reliable crimp has been applied.

Some self-expanding stents are difficult to load by hand onto a delivery device such as a catheter. Furthermore, the more the stent is handled the higher the likelihood of human error, which is antithetical to a properly crimped stent. Accordingly, there is a need in the art for a device for reliably crimping a stent onto a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, U.S. Pat. Nos. 5,437,083 and 5,546,646 to Williams et al.

Yet another stent crimping tool is known in the art as the BARD XT, which is actually a stent loader. It is constructed from a rigid, tubular body with a ball at one end connected to a plurality of long, thin strips passing through the tubular body. An uncrimped stent is placed over the plurality of long, thin strips, which hold the stent in an expanded state. The balloon portion of a catheter is inserted into the cylindrical space formed by the plurality of strips. When the user pulls the ball while holding the tubular body against the stent, the strips are slid from beneath the stent and the stent is transferred onto the balloon portion.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices are suitable for crimping stents onto balloon catheters, they suffer from problems such as non-uniform crimping forces, resulting in non-uniform crimps. Consequently, they are unsuitable for use by physicians in a cath lab who desire to crimp the stent onto the balloon catheter.

SUMMARY OF THE INVENTION

Both PTCA and PTA procedures have become commonplace in treating stenoses or lesions in blood vessels and coronary arteries. In approximately 35% to 40% of the procedures, restenosis may develop requiring a further angioplasty, atherectomy or bypass procedure to return the patency of the vessel. Intravascular stents are now being deployed after PTCA and PTA procedures, and after atherectomies, in order to help prevent the development of restenosis. Importantly, such stents, mounted on the balloon portion of a catheter, must be tightly crimped to provide a low profile delivery diameter, and to ensure that the stent stays on the balloon until the balloon is expanded and the stent is implanted in the vessel.

The present invention is directed to a crimping tool that can repeatedly provide a uniform and tight crimp to ensure the low profile diameter of the stent on the balloon portion of the catheter, and to ensure that the stent remains firmly attached until it is implanted in the vessel by expanding the balloon.

The present invention stent crimping tool is based on the mechanics of a rotational hemostatic valve (RHV). That is, the design attempts to concentrically crimp a stent onto a balloon catheter by relying on the action of three major components: a thick-walled resilient tube, a rigid but transparent housing, and a thumb screw.

In particular, in a preferred embodiment, the present invention tool comprises a thumb screw having a cylindrical shape with a first end and a second end, wherein the second end includes external threads, and wherein the second end includes a recess having a taper leading to an opening in the first end; a housing having an internal cylindrical space with first and second ends, wherein the first end of the space is open and includes threads, and wherein the second end of the space includes a taper leading to an opening; a resilient tube having a passage therethrough, the tube having tapered ends, and wherein the tube is disposed within the cylindrical space of the housing.

In the preferred embodiment, the tube is made from silicone, and the housing can be injection molded from a transparent but rigid thermoplastic material. It may also be machined out of acrylic or lexan. A transparent housing permits the physician to visually align the stent and catheter assembly with the tube just prior to undergoing the crimping step.

The present invention tool should ideally be operated by a physician in a cath lab to crimp a stent onto a balloon catheter. An uncrimped stent is positioned inside the resilient tube such that the ends are equidistant from the ends. When the tool is to be used, the physician advances the balloon catheter through the opening in the first end of the thumb screw leading into the passage of the tube. The physician then uses the balloon markers and the ends of the stent to visually aligned their relative positions. Holding the balloon catheter in place, the physician next tightens the thumb screw to the extent of its travel. This further advances and compresses the thumb screw into the tube holding the stent and balloon. The compression causes the resilient tube to decrease in length, and because of surface tension and its containment by the housing, the volume of the tube is held constant. Hence, the decrease in length results is a proportionate increase in wall thickness of the tube and conversely, a proportionate decrease in the diameter of the passage containing the stent and balloon catheter. The decrease in the diameter of the passage collapses the space and compresses the stent on to the balloon catheter.

At this point, the stent should be securely crimped on to the balloon. The thumb screw can be counter-rotated to relieve pressure on the crimped stent and balloon. The balloon with the crimped stent can then be withdrawn from or advanced through the tool. The crimped stent is now ready for implantation in a patient.

An optional mandrel can be inserted inside the balloon catheter to prevent excessive deformation of the stent during the crimping step. In an alternative embodiment, the tube can be made into at least two lengthwise-discrete segments separated by at least one annular washer. The smaller segments of the tube would offer less surface displacement during the crimping step. Yet another alternative embodiment includes at least two semicircular resilient tube halves.

Use of the thumb screw permits the physician to precisely control the amount of crimping force transmitted to the stent. With precise control of applied crimping forces, the present invention tool is capable of homogeneously crimping a stent onto a balloon catheter.

Such a crimping tool is highly useful to cardiologists, for example. Such physicians are often concerned with proper deployment of the stent within the patient that it is desirable to have a consistently and reliably crimped stent. The present invention tool is further a time saver, because the stent crimping procedure can be performed fairly efficiently and quickly.

Another advantage of this particular invention is that it is balloon friendly. In that regard, the compliance of the resilient tube can be varied so that the balloon is not damaged by the crimping of the stent onto the catheter. These and other advantages of the present invention will become apparent from the following detailed description thereof when taken in conjunction with the accompanying exemplary drawings.

DETAILED DESCRIPTION OF THE PREFERRED EMBODIMENTS

Figure 1:
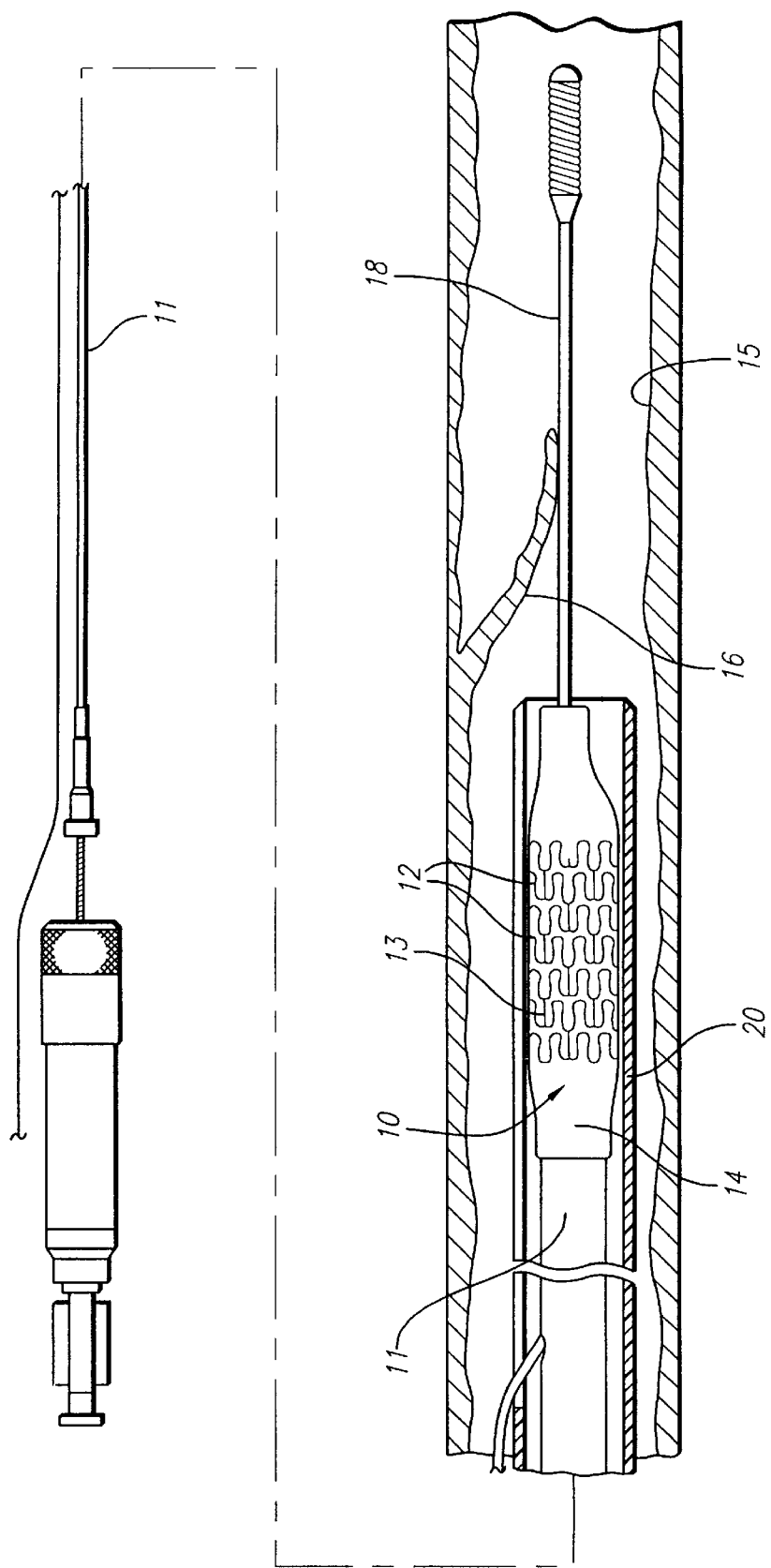
FIG. 1 is a side elevational view, partially in section, depicting a stent that has been crimped onto a delivery catheter and disposed within a vessel.

FIG. 1 illustrates intravascular stent 10 which is mounted onto delivery catheter 11. Stent 10 generally comprises a plurality of radially expandable cylindrical elements 12 disposed coaxially and interconnected by members 13 disposed between adjacent cylindrical elements 12. Delivery catheter 11 has an expandable portion or balloon 14 for expanding stent 10 within coronary artery 15 or other vessel such as saphenous veins, carotid arteries, arteries, and veins. Artery 15, as shown in FIG. 1, has dissected lining 16 which has occluded a portion of the arterial passageway.

Delivery catheter 11 onto which stent 10 is mounted is essentially the same as a conventional balloon dilatation catheter for angioplasty procedures. Balloon 14 may be formed of suitable materials such as polyethylene, polyvinyl chloride, polyethylene terephthalate and other like polymers. In order for stent 10 to remain in place on balloon 14 during delivery to the site of the damage within artery 15, stent 10 is compressed onto balloon 14.

An optional retractable protective delivery sleeve 20 may be provided to further ensure that stent 10 stays in place on balloon 14 of delivery catheter 11 and to prevent abrasion of the body lumen by the open surface of stent 10 during delivery to the desired arterial location. Other means for securing stent 10 onto balloon 14 may also be used, such as providing collars or ridges on the ends of the working portion, i.e., the cylindrical portion of balloon 14.

In order to implant stent 10, it is first mounted onto inflation balloon 14 on the distal extremity of delivery catheter 11. Stent 10 is crimped down onto balloon 14 to ensure a low profile. The present invention addresses this crimping procedure.

The catheter-stent assembly can be introduced into the patient's vasculature through processes known in the art. Briefly, guide wire 18 is disposed across the arterial section where an angioplasty or atherectomy has been performed requiring a follow-up stenting procedure. In some cases, the arterial wall lining may be detached so that guide wire 18 is advanced past detached or dissected lining 16 and the catheter-stent assembly is advanced over guide wire 18 within artery 15 until stent 10 is directly under detached lining 16. Prior to inflation of balloon 14, delivery sleeve 20 is retracted to expose stent 10. Depending on the balloon and stent assembly, a delivery sleeve may be unnecessary. Balloon 14 of delivery catheter 11 is then inflated using an inflation fluid. Expansion of balloon 14 in turn expands stent 10 against artery 15. Next, balloon 14 is deflated and catheter 11 is withdrawn leaving stent 10 to support the damaged arterial section. As mentioned above, in order to ensure proper seating of stent 10 on balloon 14, and to ensure proper deployment of stent 10 at the site of the damage within artery 15, the stent crimping procedure is important.

The present invention stent crimping tool is based on the mechanics of a rotational hemostatic valve (RHV). That is, the design attempts to concentrically crimp a stent onto a balloon catheter by relying on the action of three major components: a thick-walled resilient tube, a rigid but transparent housing, and a thumb screw.

Figure 2:
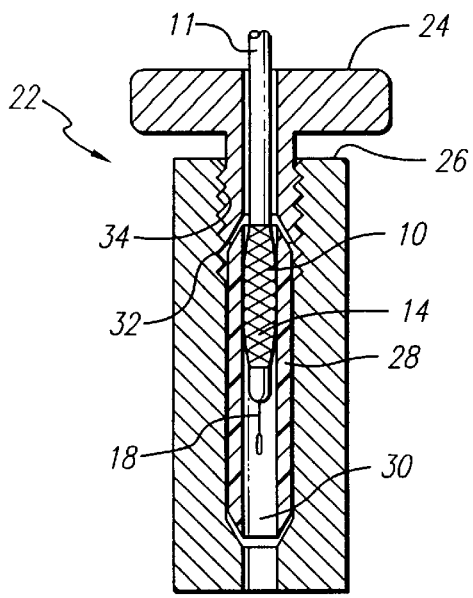
FIG. 2 is a cross-sectional view of a preferred embodiment of the present invention, showing a stent end balloon catheter positioned within a resilient tube held inside a housing with a thumb screw.
Figure 3A:
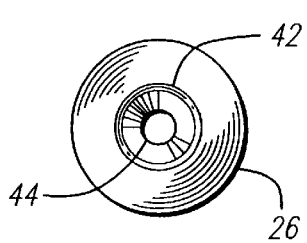
FIGS. 3A and 3B are a plan view and a side elevational view, respectively, of the present invention housing.
Figure 3B:
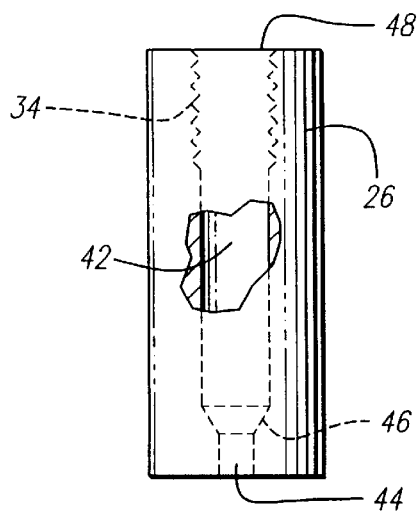

FIG. 2 provides a sectional view of a preferred embodiment of the present invention stent crimping tool 22. Stent crimping tool 22 includes thumb screw 24, housing 26, and resilient tube 28. As seen in this figure, stent 10 has already been inserted into a lumen or passage 30 of resilient tube 28. Also depicted in the drawing, balloon 14 of catheter 11 has been aligned with stent 10 and is ready for the crimping step. Although not specifically shown, stent 10 should preferably be positioned equidistant from both ends of tube 28. FIGS. 3A and 3B provide a top plan view and a side elevational view of a preferred embodiment of the present invention housing 26. Housing 26 as shown here has a cylindrical shape, but other external shapes for housing 26 are contemplated. Housing 26 has internal cylindrical space 42 leading to opening 44. In the exemplary embodiment, internal cylindrical space 42 includes a 60 degree taper 46 at one end.

Figure 4A:
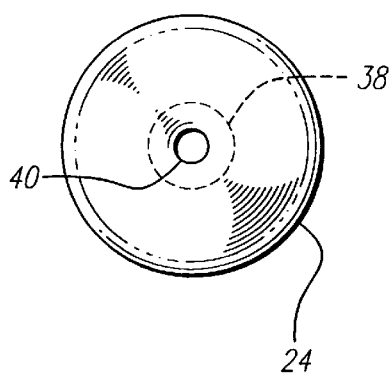
FIGS. 4A and 4B are a plan view and a side elevational view, respectively, of a thumb screw.
Figure 4B:
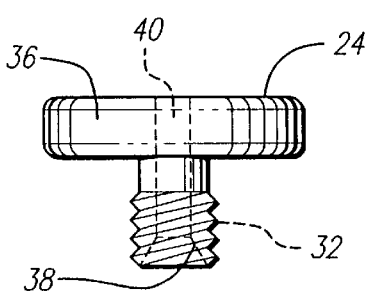

Housing 26 should preferably be made from a transparent or at least translucent material to permit the physician to visually align the balloon catheter with the premounted stent inside the present invention tool. Housing 26 should thus be injection molded from a clear or transparent thermoplastic material. It may also be machined out of clear acrylic or lexan. In an alternative embodiment, the housing may be created from materials such as lead, which offer shielding from a radioactive stent. FIGS. 4A and 4B provide a top plan view and a side elevational view of a preferred embodiment thumb screw 24 having external screw threads 32. Thumb screw 24 preferably has a two-tier, dual cylindrical shape for easier gripping by the physician. More precisely, large diameter portion 36 may have an optional textured or contoured outside diameter (not shown) to improve friction and ergonomics for the physician to apply a torque to operate the tool. Also as seen in FIGS. 4A and 4B, thumb screw 24 includes recess 38 leading to opening 40. Preferably, recess 38 has a 60 degree taper.

Figure 5A:
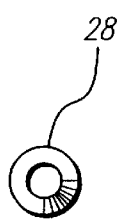
FIGS. 5A and 5B are a plan view and a side elevational view, respectively, of a resilient tube.
Figure 5B:
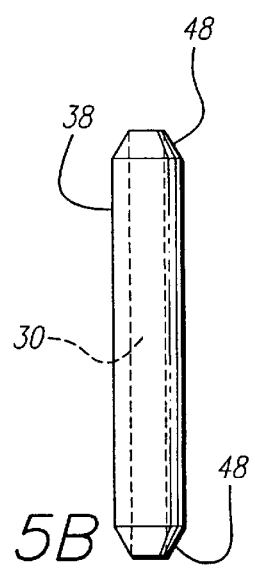

FIGS. 5A and 5B provide a top plan view and a side elevational view of a preferred embodiment of resilient tube 28. In the preferred embodiment, resilient tube 28 is made from silicone; other resilient materials known in the art are contemplated including rubber, foam, gels, etc. Furthermore, the opposite ends of tube 28 are tapered 48 at approximately 60 degrees. The tapered ends of resilient tube 28 also help in concentrating material flow to reshape tube 28 during the crimping step. Passage 30 extends through a length of tube 28. Passage 30 preferably has a diameter that approximates an outside diameter of an uncrimped stent.

All three major components depicted in FIGS. 3, 4, and 5 are assembled as shown in FIG. 2. Assembled, an exemplary embodiment of the present invention tool 22 is no larger than the existing packaging for other hand crimped stents; that is: 2 inches by 2 inches by 0.75 inch. Thumb screw 24 as mentioned above has a two-part cylinder with a maximum outside diameter of 0.75 inch and a secondary outside diameter of 0.25 inch. The inside diameter of opening 40 is a constant 0.1 inch. As mentioned earlier, to provide better gripping, the larger outside diameter of portion 36 may be patterned with indentations approximately 0.05 inch deep. In total, the length of thumb screw 24 is approximately 0.4 inch.

Tube 28, which is in contact with stent 10 and balloon 14, is preferably 0.25 inch in its outside diameter with a 0.1 inch inside diameter defining passage 30. The total length of resilient tube 28 is approximately one inch.

Housing 26 is preferably a tube cut to fit over the outside diameter of resilient tube 28. It is a clear plastic with tapped threads 34 at one end to match external threads 32 of thumb screw 24. The wall thickness of housing 26 is preferably between 0.125 inch and 0.25 inch. As mentioned above, inner cylindrical space 42 of housing 26 at one end is tapered at 60 degrees to the horizontal, and in that same end, a 0.1 inch diameter opening 44 is preferably made concentric with the center of the housing inside diameter and outside diameter.

Resilient tube 28 is placed inside internal cylindrical space 42 of housing 26. Thumb screw 24 is inserted into open end 48 of housing 26 and screw threads 32 are advanced along internal threads 34 of housing 26.

Stent 10 should already be positioned within resilient tube 28 from the cath lab or manufacturer. Tube 28 serves as a holding place for stent 10. When the physician is ready to use the tool, he or she must insert the balloon catheter through the distal end of the tool; i.e., through opening 40 of thumb screw 24. While watching through transparent housing 26, the physician then uses a balloon marker (not shown) to help align balloon 14 with the ends of stent 10. Holding catheter 11 in place, the physician then tightens thumb screw 24 to the extent of its travel.

The length of resilient tube 28 begins to decrease with the incremental advancement of thumb screw 24. Due to surface tension of resilient tube 28 and its containment within internal cylindrical space 42 of housing 26, the volume of resilient tube 28 is held constant. So as its length dimension decreases, material is displaced reshaping the walls to become thicker, which in turn decreases the inside diameter of resilient tube 28. In doing so, the inside walls of tube 28 compress stent 10 onto balloon 14. At this point in the procedure, stent 10 should be securely crimped on to balloon 14.

Next, thumb screw 24 can be rotated in the opposite direction to relieve the pressure on resilient tube 28 and in turn on the stent-balloon catheter assembly. The crimped stent-balloon catheter assembly can be withdrawn from the tool 22, or the assembly can be passed through opening 44 and advanced over guide wire 18 into the patient.

Of course, the advancement and retraction of thumb screw 24 can be repeated as necessary to ensure a consistent crimp. Also, an optional mandrel can be installed within catheter 11 to prevent over compression of stent 10 on balloon 14. Moreover, between each crimp end release cycle, it is possible to rotate the stent-balloon catheter assembly to ensure an even crimp.

Figure 6:
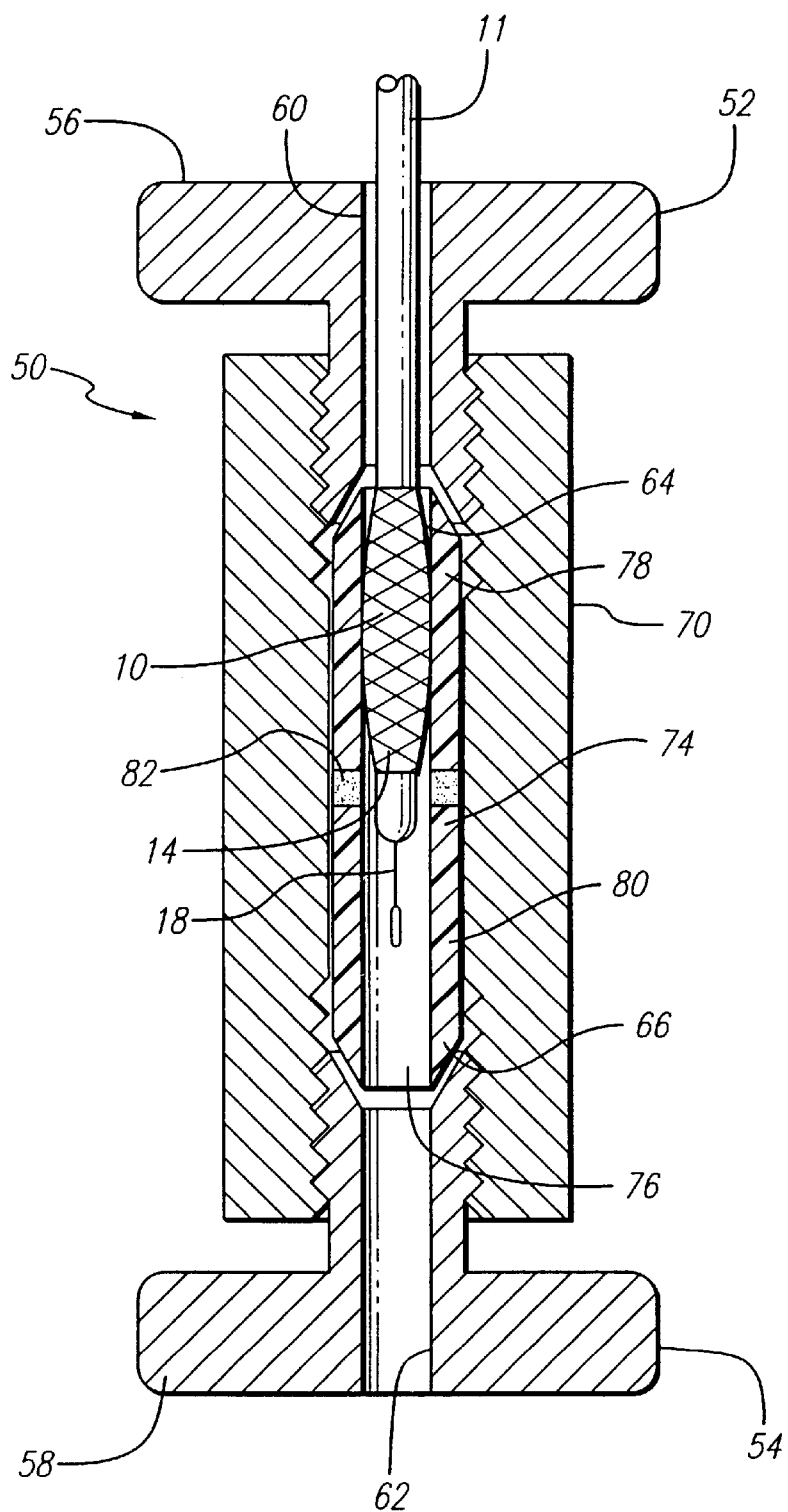
FIG. 6 is a cross-sectional view of an alternative embodiment of the present invention tool employing two thumb screws.

FIG. 6 provides a cross-sectional view of an alternative embodiment tool 50. The theory of operation is similar to the previous exemplary embodiment with the addition of a second thumb screw. As seen in FIG. 6, alternative embodiment tool 50 includes thumb screws 52, 54 having respective grippable large diameter portions 56, 58. As in the previous embodiment, thumb screws 52, 54 have respective openings 60, 62 leading to tapered recesses 64, 66. As in the previous embodiment, thumb screws 52, 54 are threaded to engage the internal threads of housing 70.

Housing 70 has an internal cylindrical space 72 that has a constant diameter from end to end, with internal threads at each end. Inside internal cylindrical space 72 is resilient tubing 74 with passage 76 containing stent 10 already loaded therein. As depicted in FIG. 6, balloon 14 of delivery catheter 11 has been aligned with stent 10 just prior to the crimping step.

In this alternative embodiment, resilient tubing 74 is broken into two discrete segments 78, 80. In between discrete segments 78, 80 is an annular washer 82. Washer 82 serves as a partition separating resilient tube 74 into its two discrete parts. One benefit is that separate discrete segments 78, 80 offer a smaller surface displacement during the crimping process. This would obviate undue friction buildup from movement of the resilient material making up resilient tube 74 as it is compressed length-wise. Yet another alternative embodiment of resilient tubing 74 includes at least two semicircular resilient tube halves.

Furthermore, operation of tool 50 is achieved by twisting thumb screws 52 and 54 alternately or simultaneously. The use of a second thumb screw and segmenting resilient tube 74 are various methods of minimizing friction on stent 10. Other methods of minimizing friction during the crimping process include: polishing the walls of passage 76, coating those walls, adding a lining to passage 76, or treating the walls through a process known in the art, etc. The goal is to minimize damage or harm to stent 10 during the crimping step.

The alternative embodiment design shown in FIG. 6 is also useful for stents having a larger length or for stents used in a multi-link system, which are very fragile. Having two thumb screws 52, 54 controls the amount of material displaced within each discrete segment 78, 80, and distributes the pressure exerted by discrete segments 78, 80 to ensure a homogeneous crimping force throughout the length of the stent.

An advantage of the present invention is that it is balloon friendly, because the compliance of resilient tube 28, 74 can be varied so that the balloon is not damaged by crimping the stent onto the catheter. Further, the present invention works best when the difference between the stent inside diameter and the balloon outside diameter is minimal, approximately 0.020 to 0.015 inch. Also from empirical experience, the present invention crimping tool may tend to slightly lengthen the stent during the crimping process.

The present invention tool is preferably sterilized and intended to be used in a cath lab by a trained technician or cardiologist. As will be appreciated by those skilled in the art, the present invention crimping tool is designed both for single use applications in a cath lab by a physician, or for multiple use applications in a sterile environment in a high volume manufacturing facility. In such a manufacturing facility where sterile conditions exist, the present invention stent crimping tool can be used repeatedly to crimp stents onto balloons until the mechanism wears out. Thus, repeated uses of the present invention are contemplated for controlled, sterile environments, as are single use applications when operated by cath lab personnel.

Furthermore, the present invention crimping tool can be used with any stent that is released without a delivery system. The crimping tool may also be sold alone, because its design is robust enough to undergo many uses.

Other modifications can be made to the present invention without departing from the scope thereof. The specific dimensions, procedural steps, and materials of construction are provided as examples, and substitutes are readily contemplated which do not depart from the invention.

What is claimed is:

1. A tool for crimping a stent on to a balloon catheter, comprising:

a thumb screw having a cylindrical shape with a first end and a second end, wherein the second end includes first threads, and wherein the second end includes a recess leading to an opening in the first end;

a housing having an internal cylindrical space with first and second ends, wherein the first end is open and includes second threads;

a resilient tube having a passage therethrough, wherein the tube is disposed within the cylindrical space of the housing;

whereby the stent is loaded inside the passage and the balloon catheter is inserted therein, and the thumb screw is threaded into the first end of the housing; and whereby turning the thumb screw advances the thumb screw, compressing the resilient tube, and crimping the stent on to the balloon catheter.

2. The stent crimping tool according to claim 1, wherein the internal cylindrical space of the housing includes a tapered second end.

3. The stent crimping tool according to claim 1, wherein the recess of the thumb screw includes a taper.

4. The stent crimping tool according to claim 1, wherein the tube has tapered ends.

5. The stent crimping tool according to claim 1, wherein the resilient tube includes silicone.

6. The stent crimping tool according to claim 1, wherein the housing is translucent.

7. The stent crimping tool according to claim 1, wherein the tube includes at least two discrete sections separated by a washer.

8. The stent crimping tool according to claim 1, wherein the tool further comprises:
- a second thumb screw having a cylindrical shape with a first end and a second end, wherein the second end includes third threads, and wherein the second end includes a recess leading to an opening in the first end;
- wherein the second end of the housing is open and includes fourth threads;
- wherein the second thumb screw is threaded into the second end; and
- whereby the second thumb screw is advanced into and compresses the tube.

9. The crimping tool according to claim 1, wherein the thumb screw includes a larger diameter portion having a patterned surface.

10. A tool for crimping a stent onto a balloon catheter, comprising:
- a thumb screw having a cylindrical shape with a first end and a second end, wherein the second end includes external threads, and wherein the second end includes a recess having a taper leading to an opening in the first end;
- a housing having an internal cylindrical space with first and second ends, wherein the first end of the space is open and includes threads, and wherein the second end of the space includes a taper leading to an opening;
- a resilient tube having a passage therethrough, the tube having tapered ends, and wherein the tube is disposed within the cylindrical space of the housing; and
- whereby the stent is loaded into the passage and the balloon catheter is inserted therein, and the thumb screw is threaded into the first end of the housing;
- whereby turning the thumb screw advances the thumb screw which compresses the resilient tube, and crimps the stent onto the balloon catheter.

11. The stent crimping tool according to claim 10, wherein the resilient tube includes silicone.

12. The stent crimping tool according to claim 10, wherein the tool further comprises a washer dividing a length of the resilient tube into two discrete segments.

13. The stent crimping tool according to claim 10, wherein the resilient tube includes a rubber.

14. The stent crimping tool according to claim 10, wherein the thumb screw includes a large diameter portion that includes a patterned surface.

15. A method for crimping a stent on to a balloon catheter, comprising the steps of:
- providing a thumb screw having a cylindrical shape with a first end and a second end, wherein the second end includes first threads, and wherein the second end includes a recess having a taper leading to an opening in the first end;
- providing a housing having an internal cylindrical space with first and second ends, wherein the first end is open and includes complementary first threads, and wherein the second end includes a tapered opening;
- providing a resilient tube having a passage therethrough, the tube having tapered ends, and wherein the tube is disposed within the cylindrical space of the housing;
- disposing the tube within the cylindrical space;
- loading the stent into the passage;
- threading the thumb screw into the first end of the housing;
- inserting the balloon catheter through the opening in the first end of the thumb screw and into the stent; and
- turning the thumb screw to advance the thumb screw into and the resilient tube, thereby crimping the stent onto the balloon catheter.

16. The method according to claim 15, wherein the thumb screw is counter-rotated to retract the thumb screw.

17. The method according to claim 15, wherein the method further comprises the steps of:
- providing an annular washer;
- separating the resilient tube into two discrete segments; and
- placing the washer in between the two discrete segments.

18. The method according to claim 15, wherein the taper in the recess approximates the taper in the resilient tube.

19. The method according to claim 15, wherein the method further comprises the steps of:
- providing a second thumb screw having a cylindrical shape with a first end and a second end, wherein the second end includes second threads, and wherein the second end includes a recess leading to an opening in the first end;
- providing an opening and complementary second threads at the second end of the housing;
- threading the second thumb screw into the second end of the housing; and
- rotating the second thumb screw into the tube.

20. The method according to claim 15, wherein the housing includes a metallic material for radioactive shielding.

* * * * *